United States Patent [19]

Haber et al.

[11] Patent Number: 4,850,953
[45] Date of Patent: Jul. 25, 1989

[54] GASTROSTOMY VALVE

[75] Inventors: Terry M. Haber, Lake Forest; William H. Smedley, Lake Elsinore, both of Calif.

[73] Assignee: Habley Medical Technology Corporation, Laguna Hills, Calif.

[21] Appl. No.: 78,102

[22] Filed: Jul. 27, 1987

[51] Int. Cl.⁴ .............................................. A61B 19/00
[52] U.S. Cl. .............................. 600/32; 128/DIG. 25; 128/887; 604/96; 604/256
[58] Field of Search .................... 604/96–103, 604/247, 256; 128/1 R, 344, DIG. 25; 600/29–32

[56] References Cited

U.S. PATENT DOCUMENTS

| | | | |
|---|---|---|---|
| 2,892,458 | 6/1959 | Auzin | 604/96 |
| 3,176,691 | 4/1965 | Ericson | 604/98 |
| 3,211,150 | 10/1965 | Foderick | 604/99 X |
| 3,915,171 | 10/1975 | Shermetta | 604/101 |
| 4,315,513 | 2/1982 | Nawash et al. | 604/175 |
| 4,344,434 | 8/1982 | Robertson | 604/247 X |
| 4,344,435 | 8/1982 | Aubin | 604/175 |
| 4,381,765 | 5/1983 | Burton | 128/1 R |

FOREIGN PATENT DOCUMENTS 822453 9/1969 Canada ................................ 604/96

Primary Examiner—Dalton L. Truluck
Attorney, Agent, or Firm—Morland C. Fischer

[57] ABSTRACT

An improved gastrostomy valve by which to deliver liquid nourishment through the abdominal wall of a baby that, due to a congenital, functional, or other disability, is unable to eat normally. The gastrostomy valve is provided with an expansible membrane or balloon and a fluid circuit interconnected therewith. Fluid is provided via the fluid circuit to inflate the balloon which, in turn, causes the membrane to roll towards the abdominal wall of a baby. The inflated membrane assumes a torroidal configuration which forms an efficient seal against the abdominal wall, whereby to minimize leakage and prevent an inadvertent removal of the gastrostomy valve from the abdominal cavity. The improved gastrostomy valve also includes an internally disposed feeding lumen or stem, an externally disposed fluid infusion port, and an anti-reflux check valve located therebetween. A connector is detachably received within the infusion port to enable a supply of liquid nourishment to be delivered from a source thereof, past the check valve, to the feeding lumen for receipt within the abdominal cavity, so as to sustain the baby and enable it to thrive.

13 Claims, 3 Drawing Sheets

GASTROSTOMY VALVE

BACKGROUND OF THE INVENTION

1. FIELD OF THE INVENTION

This invention relates to an improved gastrostomy valve which enables an external supply of liquid nourishment to be delivered through the abdominal wall of a baby who, because of congenital, functional, or other disability, is unable to eat normally.

2. PRIOR ART

As will be known to those skilled in the art, babies occasionally are unable to eat normally or to retain sufficient nourishment to survive. One reason for the foregoing disability includes esophogeal dysmotility where the baby has difficulty in swallowing. Another reason may be that the baby is mentally retarded. Yet another reason is the congenital absence of the esophogus. An additional reason is the failure to thrive or the apparent lack of appetite. A further reason may be severe gastroesphogeal reflux where the baby is constantly throwing up his food.

The prolonged inability of the baby to eat or retain nourishment can lead to severe impairment, or even death. Accordingly, gastrostomy valves are known by which to deliver an external supply of liquid nourishment through the abdominal wall of the baby. Unfortunately, the conventional gastrostomy valves are characterized by several shortcomings. Among these is the undesirable characteristic that some gastrostomy valves often leak food, enzymes, and stomach acids. Another shortcoming occurs as a consequence of the inability of many conventional gastrostomy valves to permit an adjustment of the depth to which the liquid carrying stem thereof penetrates the abdominal wall of the baby. Moreover, the conventional valves are frequently unable to be efficiently sealed against the abdominal wall. By not forming an efficient seal against the abdominal wall, reflux of food and caustic stomach fluids is often present around the stem, thereby resulting in an unsanitary condition and a potential source of irritation and discomfort to the baby.

SUMMARY OF THE INVENTION

Briefly, an improved gastrostomy valve is disclosed by which to deliver a supply of liquid nourishment to a baby that is unable to eat normally. A hollow feeding lumen or stem of the gastrostomy valve is inserted through a small incision that is made through the abdominal wall of the baby. The gastrostomy valve is provided with a fluid circuit which communicates with an expansible membrane or balloon that is wrapped around and coaxially aligned with the feeding lumen. The membrane includes a free end which is located adjacent to but detached from a distal portion of the feeding lumen and an opposite end which is bonded to a distal portion of the feeding lumen. Fluid is controllably supplied via the fluid circuit from a compressible, fluid filled bellows to simultaneously inflate the membrane and cause the free end thereof to automatically roll over the bonded end in a direction towards the baby's abdominal wall. The inflated membrane assumes a torroidal (rather than a spherical) configuration and engages the abdominal mucosa to maximize the surface area of the membrane which contacts the mucosa for retaining the gastrostomy valve within the baby's abdomen, for forming an efficient and reliable seal to prevent the leakage of food and caustic stomach fluids, and for permitting a uniform, but adjustable, pressure to be applied against the abdominal wall.

The gastrostomy valve is also provided with an externally disposed fluid infusion port which communicates with the internally disposed feeding lumen via a normally closed, anti-reflux check valve. A connector is provided to be snap fit within the infusion port. The connector supports a longitudinally extending and coaxially aligned non-coring needle. One end of the non-coring needle is placed in fluid communication with an external source of fluid nourishment by way of a fluid tube. The opposite end of the non-coring needle extends through the check valve to deliver liquid nourishment from the external source thereof to the internal feeding lumen, so that such nourishment can be received within the abdomen to sustain the baby. However, the check valve blocks the backflow of food and caustic stomach fluid through the feeding lumen.

DESCRIPTION OF THE PREFERRED EMBODIMENT

Figure 1:
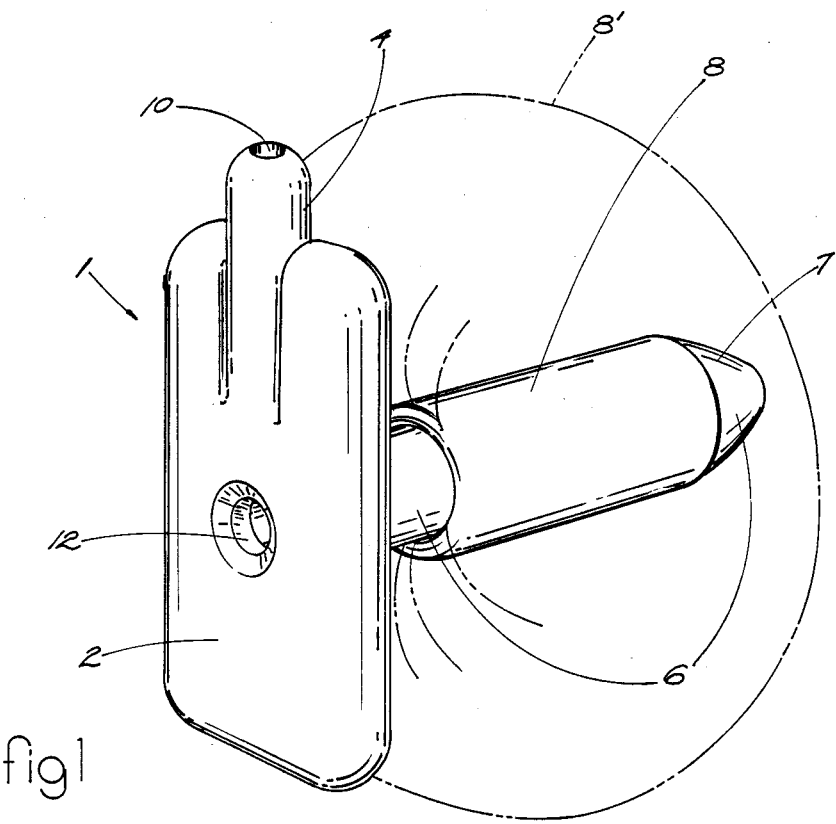
FIG. 1 is an isometric view of the gastrostomy valve which forms the present invention with an inflated membrane thereof being shown in phantom.

Referring now to the drawings, there is shown in FIG. 1 the gastrostomy valve 1 which forms the present invention. Gastrostomy valve 1 includes a planar base member 2 of generally solid cross-section, an inflation nipple 4 coextensively formed with and pivotally attached to the valve base member 2, and a hollow feeding lumen or stem 6 coextensively formed with and projecting transversely from the valve base member 2. The gastrostomy valve 1 is preferably fabricated from a suitable biocompatible material, such as silicone, or the like. An inflatable, tear-resistant membrane or balloon 8 is coaxially aligned with and wrapped around the feeding lumen 6 in an uninflated condition. Membrane 8 is preferably fabricated from an extensible, biocompatible material, such as latex, or the like. As will soon be disclosed, membrane 8 is adapted to be inflated (shown in phantom in the inflated condition and designated by reference numeral 8') after the tapered distal nose 7 of feeding lumen 6 penetrates the abdominal wall of a baby through a small incision formed therein. As will also soon be disclosed when referring to FIG. 3, and as an important detail of the present invention, membrane 8 is attached to the feeding lumen 6 in a unique manner, whereby to cause an inflated membrane 8' to simultaneously assume a torroidal (rather than a spherical)

shape while rolling towards the abdominal wall of the infant to form an efficient seal thereagainst.

A membrane inflation port 10 is formed in the inflation nipple 4 so that a suitable fluid pumping device (best shown in FIG. 3) may be placed in fluid communication with the uninflated membrane 8, whereby to controllably inflate the membrane by way of nipple 4. A fluid infusion port 12 is formed in the base member 2 of gastrostomy valve 1 so that a suitable source of liquid nourishment (best shown in FIG. 4) may be placed in fluid communication with the hollow feeding lumen 6 for controllably delivering a measured supply of sustenance to the baby.

Figure 2:
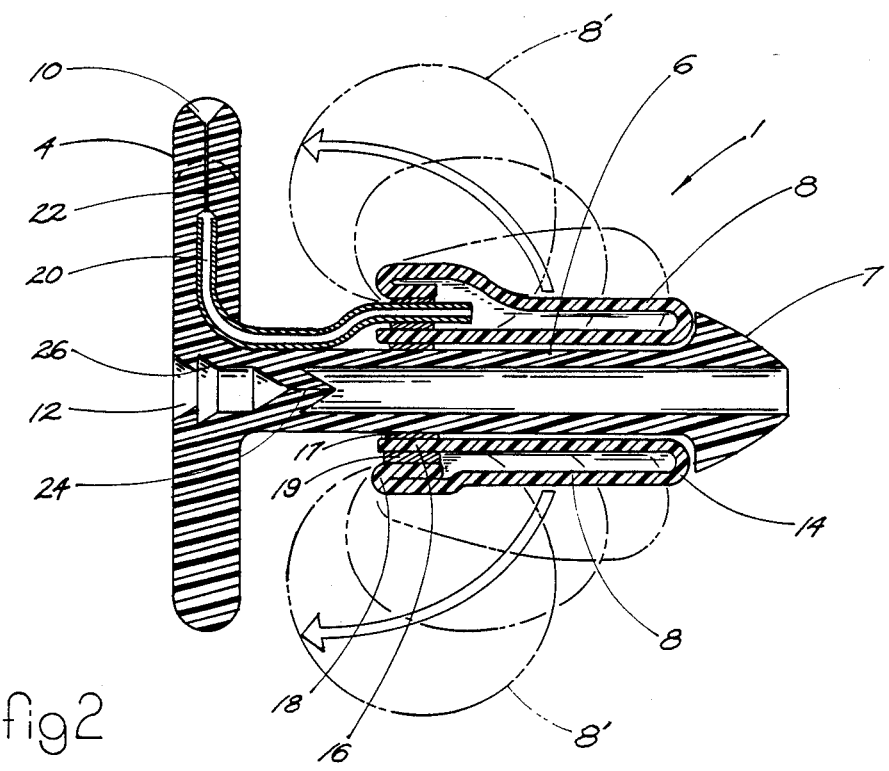
FIG. 2 shows a cross-section of the gastrostomy valve of FIG. 1.

Referring now to FIG. 2 of the drawings, details are illustrated by which the membrane 8 is attached to the feeding lumen 6 and inflated by way of inflation nipple 4. More particularly, membrane 8 includes a closed free end 14 which is located adjacent to but detached from the distal nose 7 of feeding lumen 6 and an opposite, bonded end 8 which is located adjacent and attached to the distal end of feeding lumen 6. An inner bonded end 16 of membrane 8 is attached to the proximal end of feeding lumen 6 by means of a suitable bond material 17. The outer bonded end 18 of membrane 8 is bent back upon itself and attached to the inner bonded end 16 by means of bond material 19. As will soon be explained, by virtue of the fact that only a small area (i.e. the inner bonded ends 16 and 18) of membrane 8 is attached to feeding lumen 6, and with the outer bonded end 18 bent back upon itself, a rolling, torroidal or donut-shaped balloon is formed when the membrane (designated 8' in the fully inflated condition) is inflated. That is to say, and as is best shown in FIGS. 3 and 4, an inflation of membrane 8 will permit the membrane to roll towards and be sealed against the baby's abdominal wall to prevent an inadvertent removal of the gastrostomy valve 1 from the baby's abdomen.

In order to inflate the membrane 8, one end of a hollow filling tube 20 is located in fluid communication with the interior of membrane 8 through the bonded end thereof. The opposite end of filling tube 20 extends within the inflation nipple 4 to be connected to one end of a narrow fluid channel 22 which extends through inflation nipple 4 between membrane inflation port 10 and filling tube 20. As will soon be explained in greater detail when referring to FIG. 3, inflation port 10 serves as an inlet opening through which an external supply of fluid, under pressure, is delivered for inflating the membrane.

A liquid supply of food or other nourishment is delivered through the abdominal wall of the baby way of a fluid path including fluid infusion port 12 and the hollow feeding lumen 6. An anti-reflux check valve 24 is located between infusion port 12 and feeding lumen 6. Check valve 24 prevents fluid from leaking back through feeding lumen 6 from the infant's abdomen. As will be explained in greater detail when referring to FIG. 4, fluid infusion port 12 serves as an inlet opening through which an external source of liquid food is delivered for providing nourishment to the baby. To this end, infusion port 12 is provided with docking flanges 26 by which to engage a complementary connector and thereby enable a source of such food supply to be placed in fluid communication with port 12.

Figure 3:
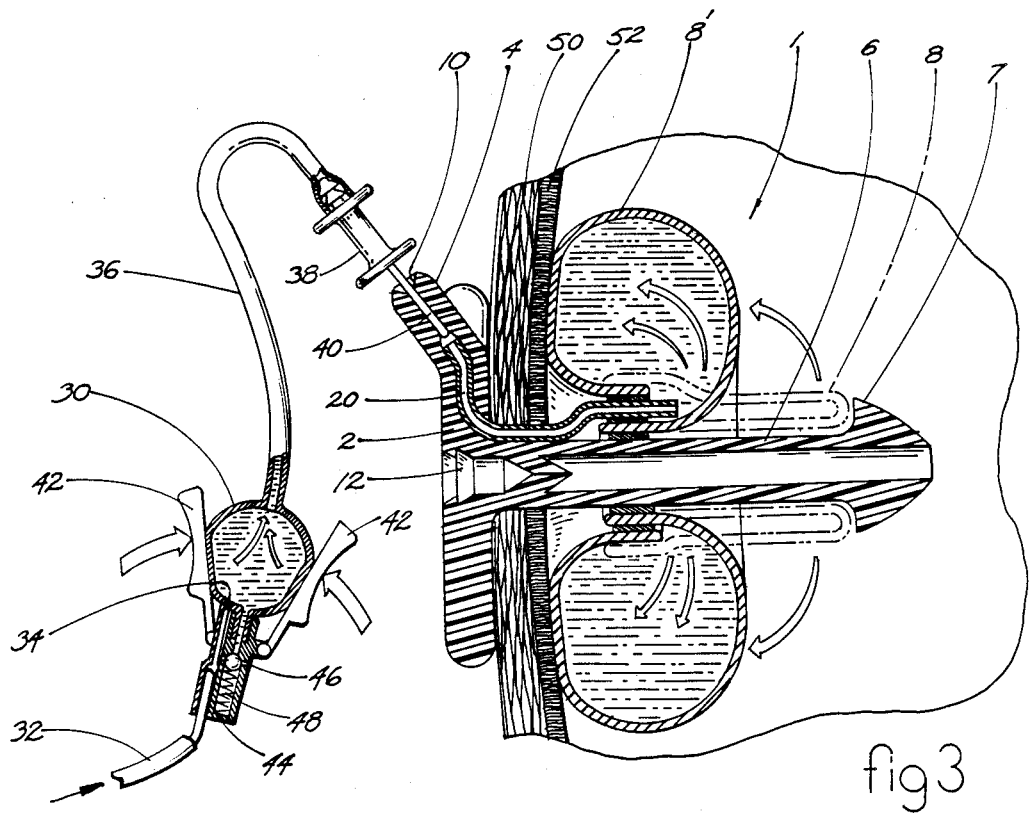
FIG. 3 shows a cross-section of the present gastrostomy valve interconnected with a compressible, fluid-filled bellows for controllably delivering fluid from the bellows for inflating the membrane.
Figure 4:
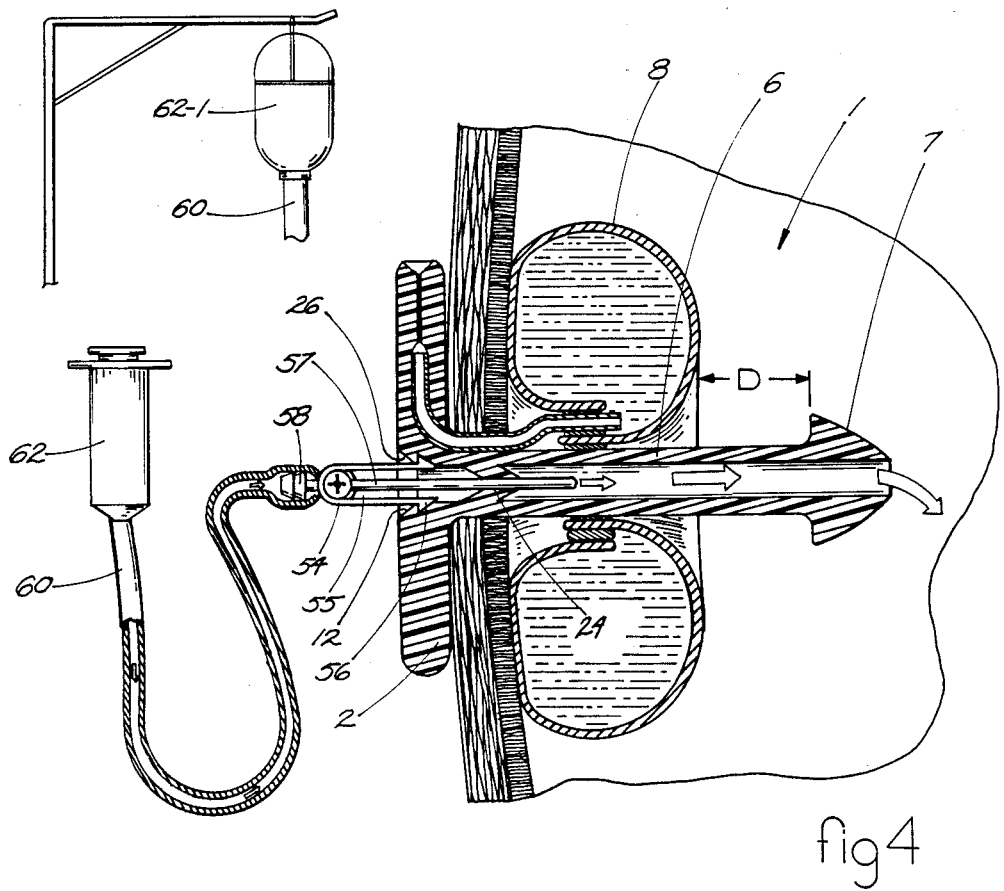
FIG. 4 is a cross-section of the present gastrostomy valve interconnected with a source of liquid nourishment for controllably delivering a supply of such nourishment through the abdominal wall of a baby.

The operation of the present gastrostomy valve 1 is now described while referring to FIGS. 3 and 4 of the drawings. In FIG. 3, a small incision is made through the abdominal wall 50 of the baby, and the tapered distal nose 7 of feeding lumen 6 is inserted therethrough, such that the uninflated membrane 8 is located at the interior of the baby's abdomen and the planar base member 2 is located at the exterior of the abdominal wall 50 (to permit easy access to inflation nipple 4 and infusion port 12). A source of fluid 30 is then placed in communication with the uninflated membrane 8 via inflation nipple 4 by which to permit inflation of the membrane (designated 8' in the inflated condition). By way of example, fluid source 30 is a compressible bellows formed from a suitable material such as silicone, or the like. Bellows 30 is filled with a supply of isotonic or iso-osmotic fluid, or the like, through a filling tube 32 and a check valve 34. A fluid path is established between bellows 30 and the uninflated membrane 8 by way of a filling tube 36 (one end of which is connected to a hollow handle 38), a non-coring needle 40 (which is connected at one end thereof to handle 38 and removably inserted at the other end thereof within the inflation port 10 of inflation nipple 4), and a filling tube 20.

A pair of rigid, manually operable, plastic pressure pads 42 are rotated into contact with the fluid filled bellows 30 to force fluid from bellows 30 into the membrane 8. A pressure relief valve 44 communicates with bellows 30 to prevent an excessive filling of the fluid path from bellows 30 to membrane 8. For purposes of convenience, pressure pads 42 are pivotally attached to the body of pressure relief valve 44. Pressure relief valve 44 preferably includes a stainless steel ball 46 which is normally biased by a compression spring 48 to block access to a plurality of outlet orifices through the body of valve 44. In the event of an overfilling of the membrane filling fluid path, the corresponding hydrostatic pressure within bellows 30 will force ball 46 rearwardly through the body of valve 44 and against the normal bias provided by spring 48 to expose the outlet orifices, whereby to permit fluid to flow outwardly therefrom and reduce the fluid volume in such path. More particularly, by virtue of pressure relief valve 44, the internal pressure within an inflated membrane can be selectively set to a level so as not to exert a pressure against the abdominal wall 50 which exceeds 80 cm of water (the approximate level of systolic blood pressure) and thereby permit the uninterrupted flow of blood.

In order to inflate the membrane 8, a physician merely depresses upon and rotates pressure pads 42 in opposite directions (as indicated by the reference arrows), whereby to compress the fluid filled bellows 30 therebetween. Accordingly, fluid is forced from the bellows 30 to the uninflated membrane 8 via fluid tubing 36, non-coring needle 10 and filling tube 20. As an important feature of the presently disclosed gastrostomy valve 1, the membrane 8 is simultaneously inflated and rolled in a direction towards the baby's abdominal wall 50. That is to say, and as was previously disclosed, by virtue of the connection of the bonded end (designated 16 and 18 in FIG. 2) of membrane 8 to the proximal end of feeding lumen 6, the free end (designated 14 in FIG. 2) of membrane 8 is automatically rolled over said bonded end and moved into engagement with the abdominal mucosa 52. What is more, and as was also previously disclosed, the inflated membrane 8' has a torroidal (rather than spherical) cross-section which advantageously maximizes the surface area thereof and provides an improved sealing geometry for contact with the abdominal mucosa 52. The inflated membrane 8' functions as an efficient and reliable mechanism for retaining the gastrostomy valve 1 within the abdomen of the baby while permitting an adjustable, but uniform, pressure to be applied to the abdominal wall 50, depending upon the thickness thereof.

In the event it becomes desirable to remove the gastrostomy valve 1 from the baby's abdomen, the physician pulls upon the handle 38, whereby to detach non-coring needle 40 from the inflation port 10 of inflation nipple 4. Hydrostatic pressure will force fluid to flow outwardly from the inflated membrane 8' to be expulsed from the gastrostomy valve 1 via filling tube 20 and inflation port 10. Accordingly, the membrane 8' is simultaneously deflated and rolled away from the abdominal wall in a direction towards the distal nose 7 of feeding lumen 6. The gastrostomy valve 1 may then be removed from the abdomen after the membrane 8 has been returned to its original, uniflated condition.

In FIG. 4, in order to supply nourishment to the baby, a source of liquid food is placed in communication with the feeding lumen 6 by means of a fluid connector which is to be received within the fluid infusion port 12 of base member 2. More particularly, the fluid connector includes a resilient, plastic body 54 having a docking catch 56 formed at one end thereof. The docking catch 56 is shaped so as to be retained in a snap fit by the docking flange 26 at the interior of fluid infusion port 12 when the connector is inserted therewithin. Extending longitudinally through the connector body 54 and being supported by a coaxially aligned spring pad 55 is a non-coring needle 57. A tubing receptacle 58 is located at one end of the non-coring needle 57 to permit needle 57 to be detachably connected to one end of a fluid tubing 60. The opposite end of fluid tubing 60 is connected to a liquid food source 62. The non-coring needle 57 is of sufficient length to extend past the docking catch 56 of connector body 54. Therefore, in the assembled relationship of FIG. 4, with the docking catch 56 of connector body 54 snapped into engagement with the docking flange 26 of fluid infusion port 12, non-coring needle 57 extends through the check valve 24 and into the feeding lumen 6. Accordingly, a one-way fluid path is established between a source 62 of liquid food and the feeding lumen 6 by means of fluid tubing 60 and non-coring needle 57.

By way of example, the source of liquid food is a hypodermically aspirated feeding means 62. However, other sources of liquid food, such as a gravity feeding bottle 62-1, may also be utilized to supply nourishment to the baby via tubing 60 and non-coring needle 57. By way of further example, the check valve 24 includes a pair of oppositely disposed lobes that normally close against one another across the interior of feeding lumen 6 (best shown in FIG. 3) to prevent fluid flow therepast. With the connector body 54 inserted within the fluid infusion port 12 of base member 2, the non-coring needle 57 extends through the interface of the lobes of check valve 24 and into the feeding lumen 6 (best shown in FIG. 4). Thus, and as illustrated by the reference arrows in FIG. 4, liquid nourishment can be supplied in a direction from source 62, through check valve 24, for receipt at the infant's abdomen. However, leakage in a reverse direction from the abdomen is prevented by the lobes of check valve 24 which extend across and block the feeding lumen 6.

By virtue of the presently disclosed gastrostomy valve 1, a physician, a parent, or one in charge of caring for a baby may easily and efficiently provide a supply of nourishment to such baby by merely snapping the resilient connector body 54 into the fluid infusion port 12.

The connector body 54 may be removed from port 12 by squeezing the connector body, so that the docking catch 56 thereof is disengaged from the docking flange 26 of infusion port 12. However, no pressure need be applied to feeding lumen 6 regardless of whether the connecting body 54 is attached to or removed from fluid infusion port 12. What is more, the depth at which the feeding lumen 6 penetrates the abdominal wall may be adjusted by controllably inflating the membrane 8'. That is, the distance, designated "D" in FIG. 4, between the inflated membrane 8' and the tapered distal nose 7 of feeding lumen 6 is inversely proportional to the volume of fluid within the membrane.

Figure 5:
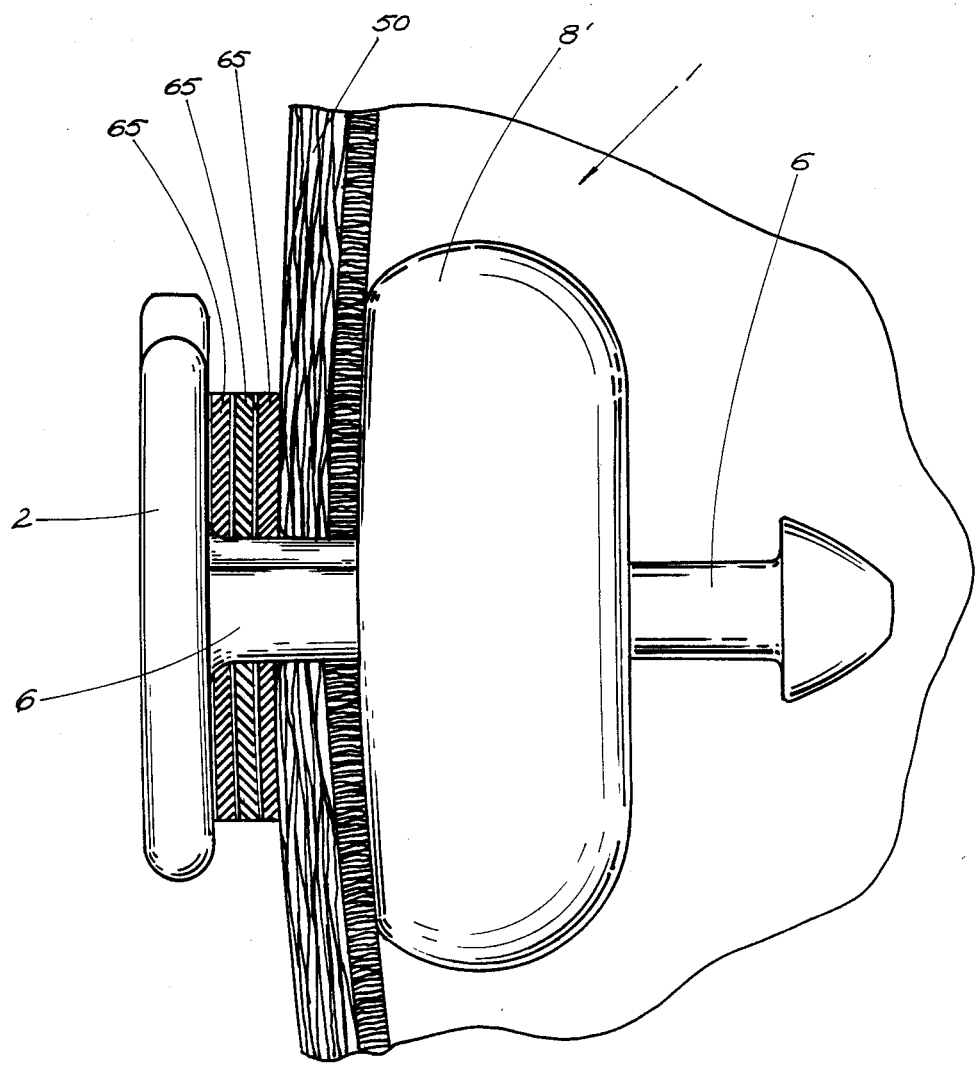
FIG. 5 shows a modification of the present gastrostomy valve including a plurality of spacer rings to accurately adjust the depth to which a feeding lumen of the gastrostomy valve penetrates the abdominal wall of the baby.

As indicated, the depth to which feeding lumen 6 penetrates the baby's abdominal wall may be adjusted by correspondingly adjusting the fluid volume of membrane 8'. However, and now referring to FIG. 5 of the drawings, one or more spacer rings 65 may also be associated with gastrostomy valve 1 to accurately control the depth to which feeding lumen 6 penetrates the abdominal wall 50. More particularly, each spacer ring 65 is a relatively flat, circular member having a centrally disposed opening by which to accommodate the feeding lumen 6 therethrough prior to the insertion of the lumen through the abdominal wall 50 of the baby. The ring 65 are preferably fabricated from a fibrous, gauze, or other absorbent material that can be treated with an antiseptic fluid. In the assembled relationship of FIG. 5, the one or more spacer rings 65 are located, as may be required according to the tissue characteristics of the baby, along feeding lumen 6 between the base member 2 and the abdominal wall 50. Therefore, an improved seal is created between the feeding lumen 6 and the abdominal wall 50. Morever, by virtue of the antiseptic nature of the spacer rings 65, the risk of infection, as a consequence of any leakage of food or stomach fluids past the inflated membrane 8', can be advantageously minimized.

It will be apparent that while a preferred embodiment of the invention has been shown and described, various modifications and changes may be made without departing from the true spirit and scope of the invention.

Having thus set forth a preferred embodiment of the invention, what is claimed is:

1. A gastrostomy valve to provide a supply of liquid nourishment from a source thereof through the abdominal wall of a recipient of said valve, said gastrostomy valve comprising an externally disposed base member and:

an internally disposed feeding lumen having proximal and distal ends and extending from said base member for delivering liquid nourishment from said source thereof to the abdoment of the recipient;

an expansible membrane surrounding said feeding lumen, a first end of said membrane being attached to a relatively proximal portion of said feeding lumen and an opposite end of said membrane being located adjacent to but detached from a relatively distal portion of said feeding lumen; and means by which to deliver a supply of fluid to the interior of said membrane to simultaneously inflate said membrane and cause the detached opposite end of said membrane to roll over the attached first end thereof in a direction towards the abdominal wall of the recipient, the inflated membrane preventing a removal of said feeding lumen from the abdomen.

2. The gastrostomy valve recited in claim 1, wherein said membrane has a torroidal shape in the inflated condition.

3. The gastrostomy valve recited in claim 1, wherein the attached end of said membrane includes inner and outer layers, said inner layer being bonded to said feeding lumen and said outer layer being turned back upon itself and bonded to said inner layer.

4. The gastrostomy valve recited in claim 1, wherein said means to deliver a supply of fluid to the interior of said membrane includes a fluid path extending between said membrane and a source of said fluid.

5. The gastrostomy valve recited in claim 4, wherein said source of fluid for inflating said membrane is a compressible bellows, said bellows having an inlet tube through which fluid is supplied thereto and an outlet tube by which to deliver the fluid from said bellows to said membrane.

6. The gastrostomy valve recited in claim 5, wherein said bellows also has a pair of manually operated pressure pads associated therewith, said pressure pads being movable in opposite directions relative to one another into contact with said bellows for compressing said bellows and forcing fluid outwardly therefrom and into said outlet tube for delivery to said membrane.

7. The gastrostomy valve recited in claim 5, wherein said bellows also has a pressure relief valve to release fluid from said bellows in the event that the volume of fluid within said bellows exceeds a predetermined level.

8. The gastrostomy valve recited in claim 4, wherein said fluid path includes:
a first fluid tube extending from said membrane to an inflation port formed in the body member of said gastrostomy valve;
a non-coring needle detachably connected at one end thereof to said inflation port to communicate with said first fluid tube; and
a second fluid tube extending between an opposite end of said non-coring needle and the source of fluid for inflating said membrane.

9. The gastrostomy valve recited in claim 1, further comprising a fluid infusion port formed in the body member of said gastrostomy valve and communicating with said feeding lumen, and a check valve located between said infusion port and said feeding lumen for controlling the flow of liquid nourishment therebetween.

10. The gastrostomy valve recited in claim 9, further comprising a connector to be detachably received within said fluid infusion port,
said connector supporting a non-coring needle, one end of which is interconnected with said source of fluid nourishment and the other end of which extends through said check valve and into said feeding lumen so that fluid nourishment is supplied from said source thereof, past said check valve, and to said feeding lumen for delivery within the abdomen of the recipient of said gastrostomy valve.

11. The gastrostomy valve recited in claim 1, further comprising at least one spacer ring extending around said feeding lumen and located between said base member and the recipient's abdominal wall to adjust the depth to which said feeding lumen penetrates said abdominal wall, said spacer ring being treated with an antiseptic material.

12. A gastrostomy valve to provide a supply of nourishment from a source thereof through the abdominal wall of a recipient of said valve, said gastrostomy valve including a base member to be located at the exterior of the abdominal wall and comprising:
a hollow feeding tube having proximal and distal ends and extending from said base member to be received through the abdominal wall of the recipient for delivering nourishment from the source thereof;
an inflatable balloon having first and second ends and positioned so as to surround said feeding tube, said first balloon end fixedly attached about a relatively proximal portion of said feeding tube, and said second balloon end located about a relatively distal portion of said feeding tube; and
means communicating with said balloon for inflating said balloon and thereby causing the second end of said inflated balloon to roll over said first end and move in a proximal direction along said feeding tube towards the abdominal wall of the recipient to prevent a removal of said feeding tube from the abdomen.

13. The gastrostomy valve recited in claim 12, wherein the second end of said balloon is located about and detached from the relatively distal portion of said feeding tube so as to be adapted to move in a proximal direction along said feeding tube and roll over said first balloon end when said balloon is inflated.

* * * * *